United States Patent [19]
Reddy et al.

[11] Patent Number: 6,110,630
[45] Date of Patent: Aug. 29, 2000

[54] EFFICIENT ACTIVATED CYANINE DYES

[75] Inventors: M. Parameswara Reddy, Brea; Maged A. Michael, Placentia; Firdous Farooqui, Brea; Naeem B. Hanna, Fullerton, all of Calif.

[73] Assignee: Beckman Coulter, Inc., Fullerton, Calif.

[21] Appl. No.: 09/100,150

[22] Filed: Jun. 18, 1998

[51] Int. Cl.$^7$ .......................... G03G 15/08; G03C 1/005; C12Q 1/68; C07H 21/00; C07D 209/56
[52] U.S. Cl. ................................ 430/93; 430/581; 435/6; 436/519; 536/25.32; 548/427
[58] Field of Search .................. 435/6; 430/581, 430/93; 436/519; 536/25.32; 548/427

[56] References Cited

U.S. PATENT DOCUMENTS

| | | | |
|---|---|---|---|
| 4,337,063 | 6/1982 | Mihara et al. | 23/230 B |
| 4,404,289 | 9/1983 | Masuda et al. | 436/538 |
| 4,405,711 | 9/1983 | Masuda et al. | 435/4 |
| 4,711,955 | 12/1987 | Ward et al. | 536/29 |
| 4,981,977 | 1/1991 | Southwick et al. | 548/455 |
| 5,047,519 | 9/1991 | Hobbs, Jr. et al. | 536/23 |
| 5,151,507 | 9/1992 | Hobbs, Jr. et al. | 536/23 |
| 5,242,796 | 9/1993 | Prober et al. | 435/6 |
| 5,268,486 | 12/1993 | Waggoner et al. | 548/427 |
| 5,348,868 | 9/1994 | Reddy et al. | 435/91.1 |
| 5,428,148 | 6/1995 | Reddy et al. | 536/26.8 |
| 5,486,616 | 1/1996 | Waggoner et al. | 548/217 |
| 5,491,059 | 2/1996 | Whitcomb | 430/618 |
| 5,569,587 | 10/1996 | Waggoner et al. | 435/6 |
| 5,569,766 | 10/1996 | Waggoner et al. | 548/150 |
| 5,627,027 | 5/1997 | Waggoner et al. | 435/6 |

FOREIGN PATENT DOCUMENTS

| | | |
|---|---|---|
| 0800831 A1 | 10/1997 | European Pat. Off. . |
| 3912046 A1 | 3/1990 | Germany . |
| 2317951 | 4/1998 | United Kingdom . |

OTHER PUBLICATIONS

Bhat, V., et al., "A Simple and Convenient Method for the Selective N–Acylations of Cytosine Nucleosides", *Nuclosides & Nucleotides*, 8(2):179 (1989).

Ernst. L.A., et al., "Cynanine Dye Labeling Reagents for Sulfhydryl Groups", *Cytometry*, 10:3 (1989).

Fieser, et al., *Reagent for Organic Synthesis*, vol. 1, 485–6, (1967).

Mujumder, R.J., et al., "Cyanine Dye Labeling Reagents: Sulfoindocyanine Succinimidyl Esters", *Bioconjugate Chemistry*, 4(2):105 (1993).

Mujumder, S.R., et al., "Cyanine–Labeling Reagents: Sulfobenzindocyanine Succinimidyl", *Bioconjugate Chemistry*, 7(2):356 (1996).

*Primary Examiner*—Jezia Riley
*Attorney, Agent, or Firm*—William H. May; Margaret A. Kivinski

[57] ABSTRACT

Activating groups based on N-hydroxynaphthalimide, are disclosed herein. The activating groups can mediate the coupling of labeling moieties, such as biotin or cyanine dyes, to a variety of components, including chain terminators, nucleoside triphosphates, and oligonucleotides, which are used in nucleotide sequencing. From these activating groups, activated esters of the labeling moieties can be prepared. The activated esters react with a component, for example a derivatized nucleotide chain terminator, to give a labeled component. In additions, methods of the present invention provide for labeling a nucleoside triphosphate in organic media. The activating groups and methods of the present invention allow the activation and coupling reactions to occur at a much higher yield, compared with the prior art.

33 Claims, 8 Drawing Sheets

Cyanine Monoacid Active Esters

Cyanine Monoacid Active Esters

Preparation of Cy5 Monoacid Active Esters

Preparation of Cy7 Monoacid Active Esters

Preparation of DBCy5 Monoacid Active Esters

Preparation of DBCy7 Monoacid Active Esters

Spectrophotometric Analysis of Cy5 Labeled 24 mer

Spectrophotometric Analysis of Cy7 Labeled 24 mer

Capillary Electrophoresis of Cy5 Labeled 24 mer

Scheme for the Synthesis of Sulpho-N-Hydroxynaphthalimide

EFFICIENT ACTIVATED CYANINE DYES

FIELD OF INVENTION

This invention relates to the general field of activating groups and is particularly concerned with N-hydroxynaphthalimide, substituted derivatives, and compounds having similar dicarbonyl structural arrangements as an activating group and methods of use.

BACKGROUND

The need for simple and efficient methods of labeling oligonucleotides has been present ever DNA synthesis became a routine laboratory procedure. Initially, practically all oligonucleotide labeling was radioactive in nature, involving a fairly straightforward enzymatic reaction consisting of adding a radioactive phosphate group from a nucleoside triphosphate, usually to the 5' end of the oligonucleotide.

However, the rapidly increasing cost of radioactive waste disposal together with an increased awareness of the potentially harmful effects of exposure to radiation have contributed to shifting the emphasis toward other ways of labeling synthetic oligonucleotides. In addition, the number of different applications where non-radioactively labeled oligonucleotides and nucleotides are being used has expanded significantly. Fluorescent In Situ Hybridization (FISH), sequencing, enzymatic amplification, and sandwich assays in microtiter plate format are but some of the applications where non-radioactively labeled oligonucleotides and nucleotides are useful.

Currently, nucleotides and synthetic oligonucleotides are generally labeled non-radioactively with two types of markers: "biological" moieties, such as biotin, Horse Radish Peroxidase (HRP), etc., and "chemical" moieties, such as fluorescent (e.g., Fluorescein, Rhodamine, etc.) or chemiluminescent (e.g. Lanthanides) groups, which have the advantage of being more readily detected.

The use of fluorescent labels with antibodies, DNA probes, biochemical analogs, lipids, drugs, cytokines, cells and polymers has expanded recent years. The wider use of fluorescent probes results partly from the evolution of advanced detection instrumentation, particularly electronic imaging microscopes and flow cytometry and partly from the availability of new fluorescent labeling reagents.

Cyanine and related dyes are "chemical" moieties, which have several desirable properties for use as sensitive detection labels. These dyes are strongly light absorbing and highly luminescent. They can be covalently attached to proteins and other biological and nonbiological markers to make these materials fluorescent so that they can be detected. The labeled materials can then be used in assays employing excitation light sources and luminescence detectors. Avidin labeled with cyanine type dyes can be used to quantify biotinylated materials and antibodies conjugated with cyanine-type dyes can be used to detect and measure antigens and haptens. Furthermore, cyanine-conjugated lectins can be used to detect specific carbohydrate groups. Moreover, cyanine-conjugated fragments of DNA or RNA can be used to identify the presence of complementary nucleotide sequences in DNA or RNA. The cyanine dyes have the advantage that by synthesizing structural modifications of the chromophore portion of the molecule, different fluorescent labeling reagents can be made that will absorb and fluoresce light at many different wavelengths in the visible and near infrared region of the spectrum. Also, the cyanine and related dyes have an advantage in that they can be synthesized with a variety of functional groups attached. This versatility permits control over such factors as the solubility of the dye and labeled product and helps reduce non-specific binding of the labeled material to irrelevant components in an assay mixture. This versatility also allows for selection of labeling reagents that minimally perturb the function of the labeled product.

Further desirable properties of these dyes include absorbance at longer wavelengths (which can translate into using inexpensive detection systems and low background from biological samples at these wavelengths), high extinction coefficients, relatively high quantum efficiencies, small molecular size, ease of chemical manipulation without compromising the fluorescence characteristics, and reasonable stability to reagents, pH, and temperature.

One of the major issues related to fluorescent labeling of oligonucleotides is the availability of fluorescent dyes in one or another chemical form, which would make it sufficiently user-friendly. Ideally, the chosen fluorescent tag would be available as a fully protected, modified CED-phosphoramidite. This would allow the user to simply load the labeled phosphoramidite resuspended in acetonitrile, at the extra base position (X-bottle) on a DNA synthesizer. Using the "labeling" method on the instrument would result in the direct and efficient incorporation of the label at the desired position in the oligonucleotide being synthesized. The advantage of this approach is that the number of steps involved in obtaining the labeled oligonucleotide is significantly reduced compared to indirect labeling methods. The major inconvenience is that this method implies the use of dye phosphoramidites, which are substantially more expensive and less stable, particularly to cleavage and deprotection conditions, than their standard, unmodified counterparts.

Accordingly, an indirect labeling method should be used when the chosen fluorescent tag is not available as a modified phosphoramidite. This method would still require that the fluorescent tag be presented under a form compatible with easy coupling to the synthetic oligonucleotide. The problem is not trivial, since OH groups are not very good receiving moieties in coupling reactions, and particularly since an oligonucleotide normally features two OH groups, (one at the 3' end, the other at the 5' end). In applications such as sequencing and PCR, the 5' end or any other position but the 3' end should be labeled.

For the time being, the indirect labeling method requires the incorporation of a primary amino group, most of the time at the 5' end of the oligonucleotide. This is typically achieved by adding a so-called amino-link or amino-modifier phosphoramidite as the last step in the synthesis, using the "labeling" method on the synthesizer. Some purification is needed thereafter, prior to setting up the actual coupling reaction with the fluorescent tag. The major advantage of this approach is that, once purified and 5' deblocked, the amino-oligonucleotide preparation can be further labeled according to the user's specific needs.

Typically, the fluorescent tag is added as an activated moiety, e.g., NHS-ester, to a nucleotide or oligonucleotide into which a primary amino group has been incorporated, usually at the 5' end. N-hydroxysuccinimidyl esters are well known as reactive groups, however their yields and stability in aqueous media are not often optimal. Other alternatives include the use of carbodiimides, anhydrides, and other active esters, such as paranitrophenol, to activate carboxyl groups of the fluorescent dye molecule. The less desirable aspects of existing methodologies can include a lack of selectivity of the activated product for nitrogen nucleophiles over competing species, their relative complexity to prepare (and hence their reduced cost-effectiveness), the relative lability of the activated product under coupling conditions.

For the foregoing reasons, there exists a need for novel methods to activate fluorescent dyes, for indirect methods of labeling oligonucleotides, which overcome the difficulties of the prior art. Furthermore, the method can be used to label nucleotides and oligonucleotides with a variety of fluorescent tags, including cyanine dyes, which are presently unavailable in forms suitable for direct labeling methods. Still further, there exists a need for methods of labeling nucleotides and oligonucleotides in both organic and aqueous solvents.

SUMMARY

The present invention is directed to the synthesis and use of N-hydroxynaphthalimide activated derivatives and compounds having similar dicarbonyl structural arrangements as activating groups that meets the above-mentioned needs. A method of labeling components using N-hydroxynapthalimide and substituted derivatives is also provided. Also disclosed are activated cyanine dyes and a method of synthesizing the activated dyes. Further, simple straightforward methods for labeling oligonucleotides, nucleotide triphosphates and dideoxynucleotide triphosphate terminators are provided. The activated dyes make it possible to label oligonucleotides with cyanine dyes, which have several desirable properties such as absorbance at longer wavelengths, high extinction coefficients, relatively high quantum efficiency, and reasonable stability to reagents, pH, and temperature. Moreover the method of attaching the use N-hydroxynaphthalimide of cyanine dyes to an oligonucleotide is selective for nitrogen and thiol nucleophiles over competing species such as water or hydroxyl groups. Accordingly, the compound is ideally suited for indirect labeling techniques utilizing modified amino-nucleotides. Still further, a method of converting compounds to their trialkyl ammonium salts is provided making the above methods versatile to use in both aqueous and organic solvents.

It is an object of the present invention to provide an activated dye having the formula:

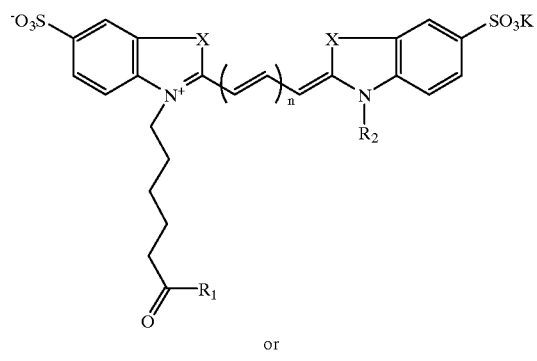

or

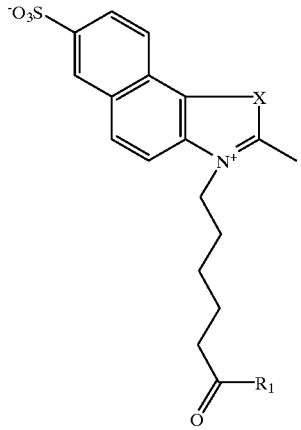

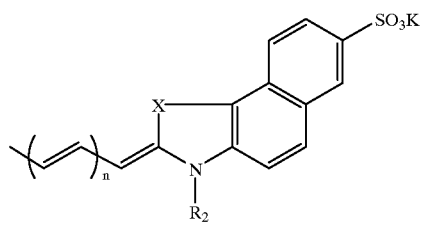

wherein n is 1, 2, or 3, X is S, O, N, $CH_2$, or $C(CH_3)_2$, R1 is N-oxynaphthalimide-Rx, and R2 is alkyl, alkylsulfonate, alkylcarboxylate, activated alkylsulfonate, or activated alkylcarboxylate having an alkyl chain about one to ten carbon atoms long, whereby Rx is selected from the group consisting of hydrogen, sulfonyl and alkyl.

Also provided, according to another embodiment of the present invention is a method of preparing an activated dye. The method comprising the steps of dissolving a cyanine dye having at least one carboxyl group in a solvent, and combining N-hydroxynaphthalimide-Rx and an activating agent, such as carbodiimidazole (CDI) or dicyclohexylcarbodiimide (DCC), with the dissolved cyanine dye to form an activated dye. Rx is selected from the group consisting of hydrogen, sulfonyl and alkyl.

Preferably, the cyanine dye is selected from the group consisting of Cy5, benzo-Cy5, dibenzo-Cy5, Cy7, benzo-Cy7, and dibenzo-Cy7 and other cyanine dyes having extended aromatic ring structures.

Typically, the solvent comprises an organic solvent. Preferably, the solvent comprises dimethyformamide.

Typically, the amount of N-hydroxynaphthalimide-Rx combined with the cyanine dye is at least about 2 molar equivalents. Preferably, the amount of N-hydroxynaphthalimide-Rx ranges from about 1.5 to about 5 molar equivalents.

The method can further comprise the additional step of precipitating the activated dye from the mixture. Preferably, the activated dye is precipitated by adding ethyl acetate.

In yet another embodiment of the present invention, there is provided a method of labeling an oligonucleotide, comprising:

modifying an oligonucleotide to contain a nucleophile, thereby forming a modified oligonucleotide;

combining the modified nucleotide with an activated dye having at least one N-oxynaphthalimide-Rx group, wherein Rx is selected from the group consisting of hydrogen, sulfonyl and alkyl.

Typically, the modified oligonucleotide is an amino-oligonucleotide.

Preferably, the activated dye is selected from the group consisting of:

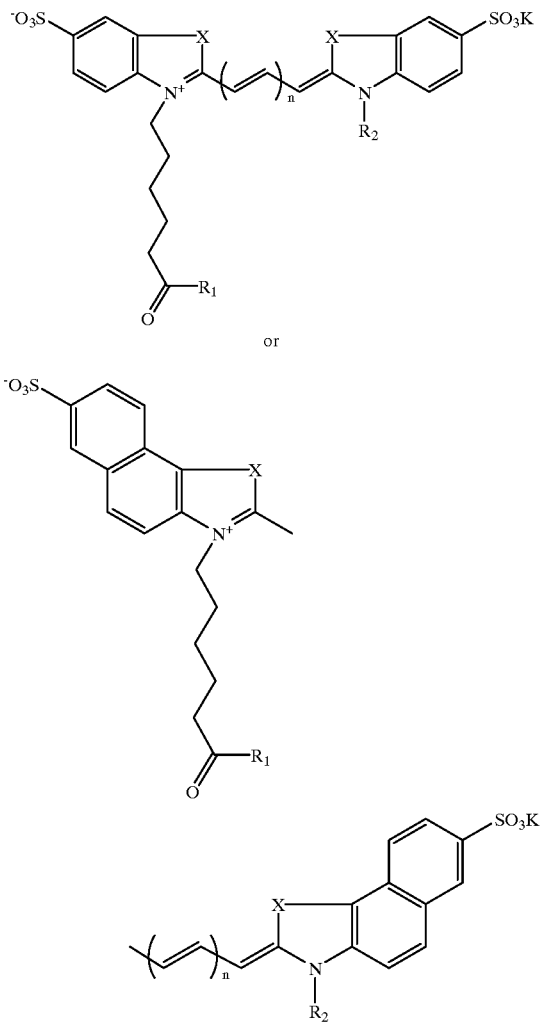

or wherein n is 1, 2, or 3, X is S, O, N, $CH_2$, or $C(CH_3)_2$, R1 is N-oxynaphthalimide-Rx, and R2 is alkyl, alkylsulfonate, alkylcarboxylate, activated alkylsulfonate, or activated alkylcarboxylate having an alkyl chain about one to ten carbon atoms long, whereby Rx is selected from the group consisting of hydrogen, sulfonyl and alkyl.

The activated dye typically is combined in molar excess relative to the modified nucleotide.

In yet another embodiment of the present invention, there is provided a method of labeling a component comprising, combining the component with an activated moiety having at least one N-hydroxynapthalimide-Rx group, wherein Rx is selected from the group consisting of hydrogen, sulfonyl and alkyl.

Typically, the component is selected from the group consisting of nucleosides, nucleotides, nucleoside triphosphates, dideoxynucleoside triphosphates, deoxy-nucleoside triphosphates, and derivatized versions of the foregoing. Further components include nucleic acids, DNA, derivatized nucleic acids, derivatized deoxynucleic acids, DNA fragments, RNA fragments, derivatized DNA fragments, and derivatized RNA fragments. Components can also include antibodies, proteins, peptides, enzyme substrates, hormones, lymphokines, metabolites, receptors, antigens, haptens, lectins, avidin, streptavidin, toxins, carbohydrates, oligosaccharides, polysaccharides, and other materials including drugs, toxins, blood cells, microbial materials, particles, plastic or glass surfaces, and polymer membranes.

The activated moiety typically can be biotin, hapten, cyanine dyes, merocyanine dyes, styryl dyes, fluorophores such as fluorescein, rhodamine, Texas red, chemiluminescent molecules such as acridinium esters, dioxitane derivatives, electroluminescent labels such as ruthenium based molecules, hapten molecules such as digoxigenin, chromophore molecules such as coumarins and other detection molecules.

Also provided according to the present invention is a method of labeling a nucleotide triphosphate. The method includes the steps of, converting the nucleoside triphosphate to its trialkyl ammonium salt to form a nucleoside triphosphate trialkyl ammonium salt, and combining the nucleoside triphosphate trialkyl ammonium salt with an activated moiety having at least one activated ester, preferably an N-oxynaphthalimide-Rx group, wherein Rx is selected from the group consisting of hydrogen, sulfonyl and alkyl.

Preferably, the activated moiety is selected from the group consisting of biotin, hapten, cyanine dyes, merocyanine dyes, styryl dyes, fluorophores such as fluorescein, rhodamine, Texas red, chemiluminescent molecules such as acridinium esters, dioxitane derivatives, electroluminescent labels such as ruthenium based molecules, hapten molecules such as digoxigenin and chromophore molecules such as coumarins.

Preferably, the method is done in an organic solvent.

Also provided is a method of preparing a dye labeled dideoxynucleoside triphosphate terminator. The method includes the steps of combining in a reaction mixture, a tributyl ammonium salt of a nucleoside triphosphate terminator, and an activated dye having at least one N-oxynapthalimide-Rx group.

BRIEF DESCRIPTION OF THE DRAWINGS

These and other features, aspects, and advantages of the present invention will become better understood with reference to the following description, appended claims, and accompanying drawings where:

DESCRIPTION

The present invention is directed to the synthesis and use of N-hydroxynaphthalimide, substituted derivatives, and compounds having similar dicarbonyl structural arrangements as activating groups that meet the above-mentioned needs. A method of labeling components using N-hydroxynapthalimide and substituted derivatives is also provided.

The present invention pertains to methods for covalently attaching luminescent cyanine and cyanine-type dyes to biological materials, non-biological molecules and macromolecules, and particles in order to make the material that has been labeled luminescent so that the labeled material can be detected and/or quantified by luminescence detection methods.

Further, simple straightforward methods for labeling oligonucleotides, nucleotide triphosphates and dideoxynucleotide triphosphate terminators are provided. The activated dyes make it possible to label oligonucleotides with cyanine dyes, which have several desirable properties such as absorbance at longer wavelengths, high extinction coefficients, relatively high quantum efficiency, and reasonable stability to reagents, pH, and temperature. Moreover, the method of attaching N-hydroxynaphthalimide activated cyanine dyes to an oligonucleotide is selective for nitrogen and thiol nucleophiles over competing species such as water or hydroxyl groups. Accordingly, the compound is ideally suited for indirect labeling techniques utilizing modified amino-nucleotides. Still further, a method of converting compounds to their trialkyl ammonium salts is provided making the above methods versatile to use in both aqueous and organic solvents.

In one aspect according to the present invention, cyanine dyes have been developed having substituent groups which are covalently reactive under suitable reaction conditions with amine (—NH$_2$), hydroxy (—OH), and sulfhydryl groups on proteins and other materials for purposes or fluorescence and phosphorescence detection of those materials. Furthermore, amine, hydroxy, and sulfhydryl groups can be easily added to components such as polymer particles, which do not naturally contain either sulfhydryl, amine or hydroxy groups, prior to labeling with activated cyanine dyes.

The present invention relates to the labeling, with N-hydroxynapthalimide activated cyanine dyes, of nucleosides, nucleotides, oligonucleotides, proteins and other materials, including nucleic acids, DNA, drugs, toxins, blood cells, microbial materials, particles, etc. at an amine, sulfhydryl, or hydroxy site on those materials. The dyes are advantageously soluble in aqueous or other medium in which the labeled material is contained.

Figure 1:
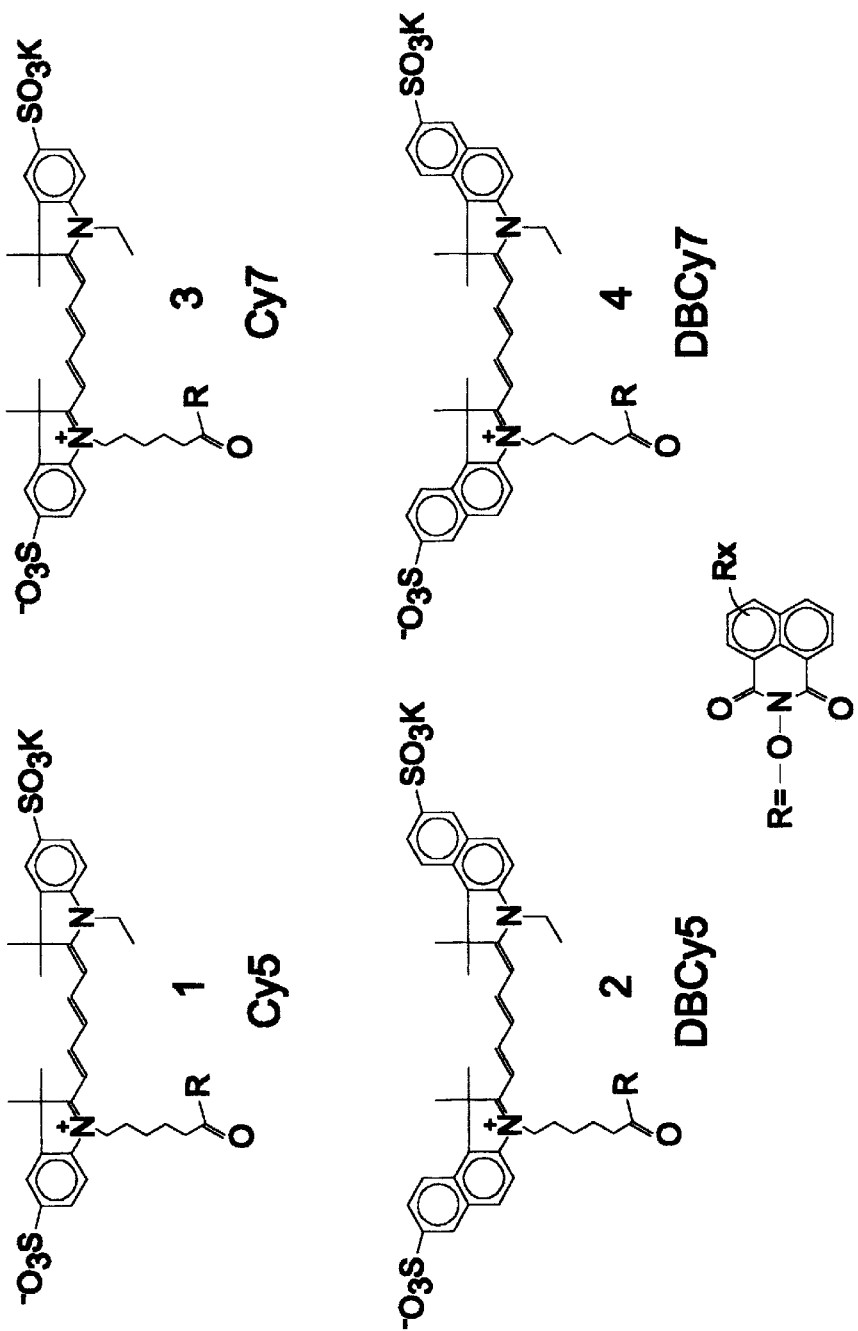
FIG. 1 shows structural formulas of four Cyanine Mono Acid active esters, Cy5, DBCy5, Cy7 and DBCy7, which includes N-oxynapthalimide as the activating group.
Figure 2:
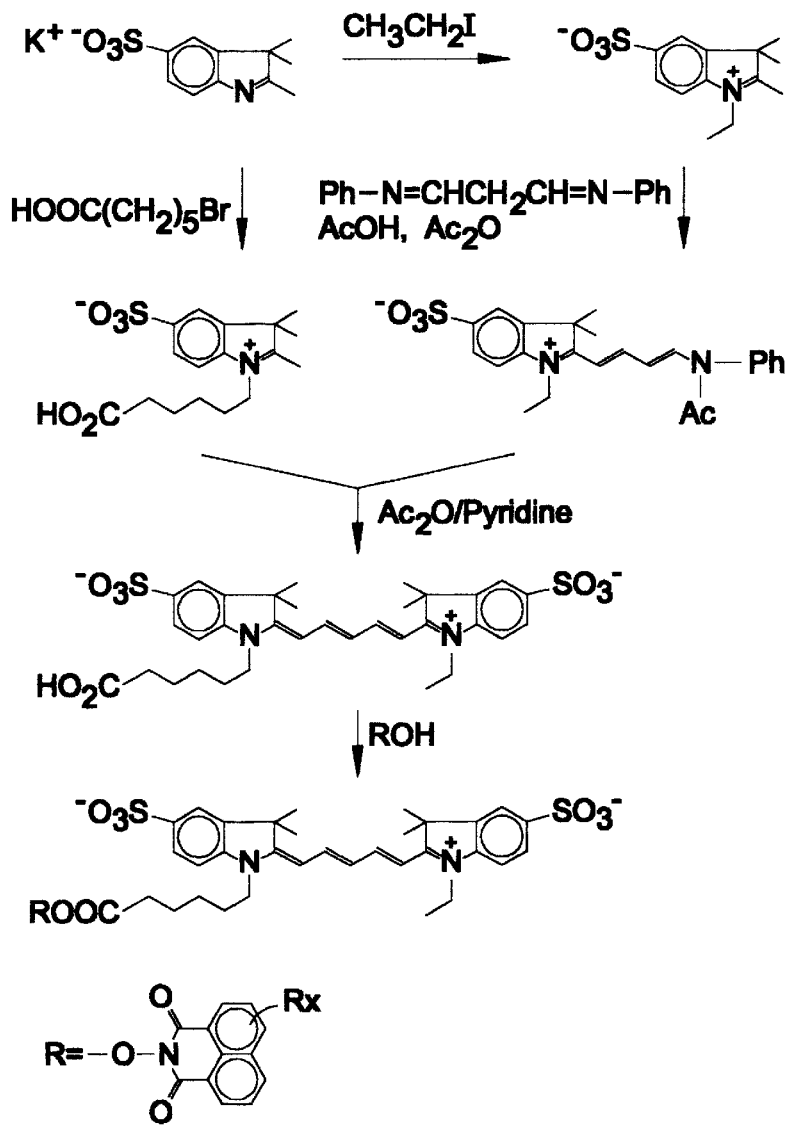
FIG. 2 is a schematic diagram outlining the steps for the preparation of Cy5 Monoacid Active Ester.
Figure 3:
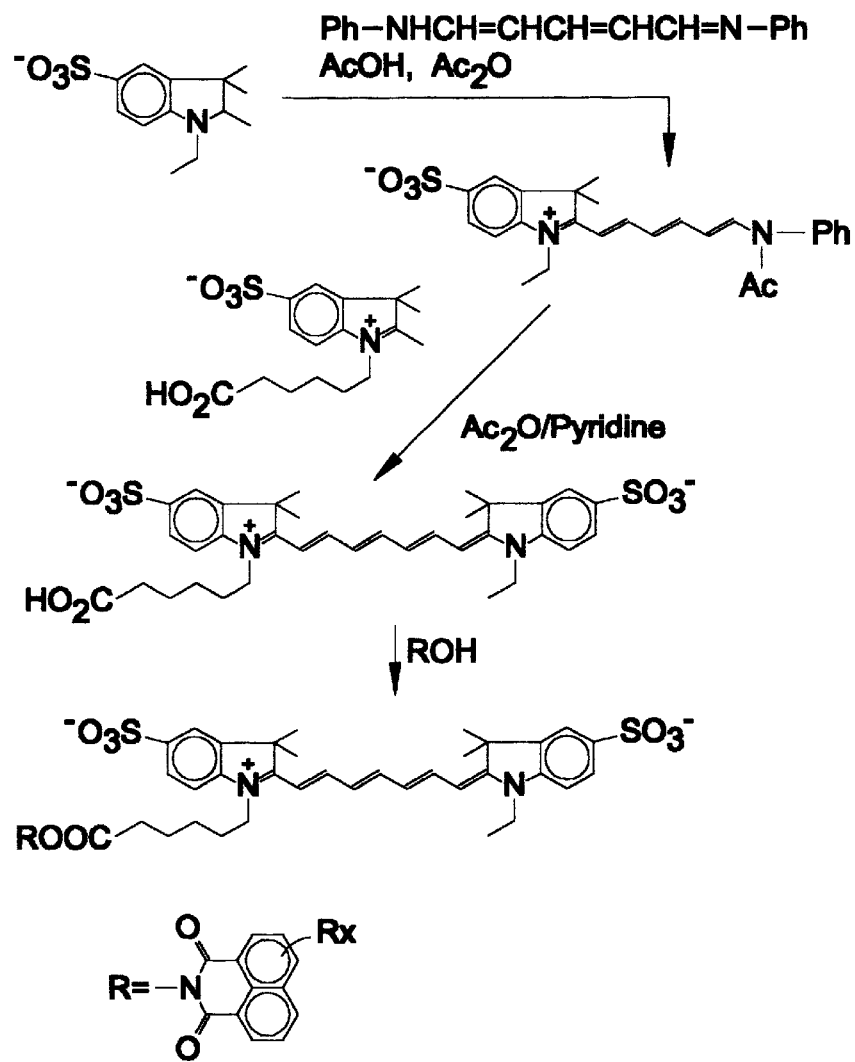
FIG. 3 is a schematic diagram outlining the steps for the preparation of Cy7 Monoacid Active Ester.
Figure 4:
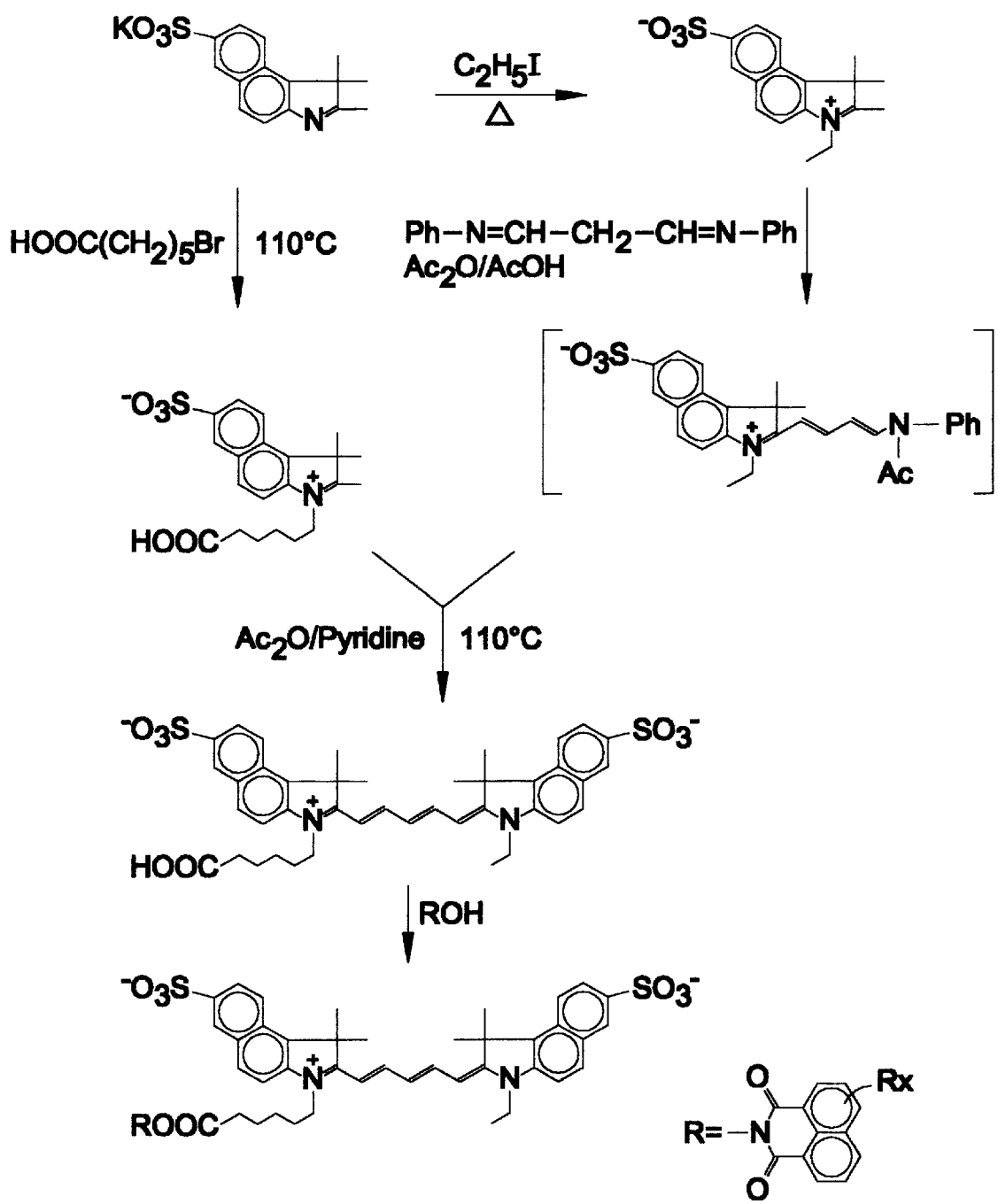
FIG. 4 is a schematic diagram outlining the steps for the preparation of DBCy5 Monoacid Active Ester.
Figure 5:
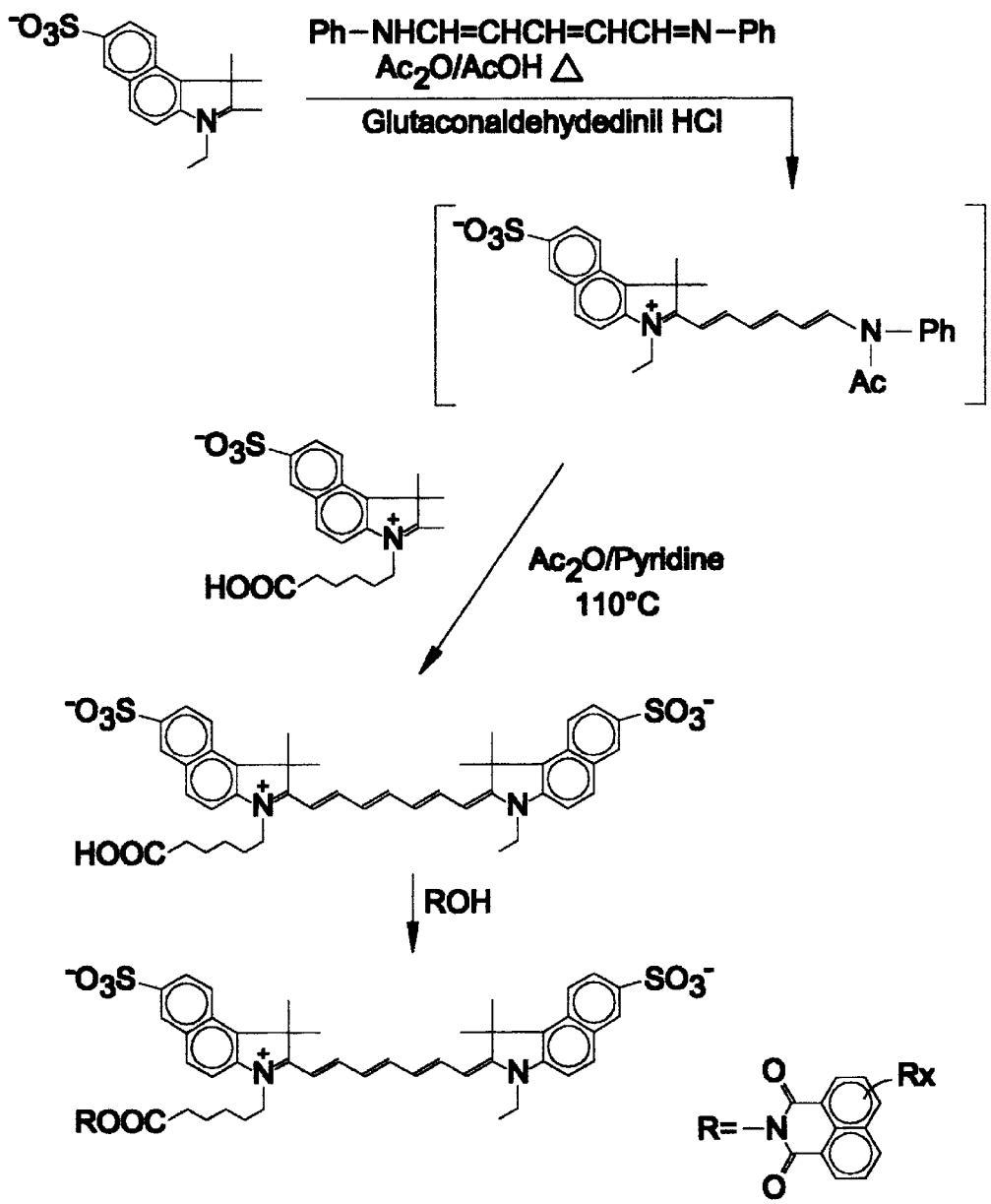
FIG. 5 is a schematic diagram outlining the steps for the preparation of DBCy7 Monoacid Active Ester.

The following references are incorporated herein by reference in their entirety, including cited references. These references are related to reactive Cyanine dyes which are described in the following patents for other uses: Mihara et al. (U.S. Pat. No. 4,337,063), and Masuda et al. (U.S. Pat. Nos. 4,404,289; 4,405,711) have synthesized a variety of cyanine dyes possessing N-hydroxysuccinimide active ester groups. See also, Waggoner et al. (U.S. Pat. Nos. 5,486,616; 5,569,587; 5,569,766; and 5,627,027)
N-hydroxynaphthalimide esters Typically, in primer labeling, cyanine dye N-hydroxysuccinimide esters can give low yields when conjugated to oligonucleotides. In order to improve the conjugation yields, N-hydroxynaphthalimide was found to be an efficient leaving group. This group has unique properties of having the desired stability in aqueous media in which the conjugation reactions are performed, yet being sufficiently reactive with the amino oligonucleotide, thus resulting in very high yields. The uniqueness may presumably be due to its structure where two carbonyl groups form a six-membered ring, which is attached to two aromatic rings. In contrast, the two carbonyl groups of N-hydroxysuccinimide form a five-membered ring. Similarly, both carbonyls of N-hydroxyphthalimide form a five-membered ring, which is attached to one aromatic ring. The structures of the most preferred N-hydroxynaphthalimide activated cyanine dyes are depicted in FIG. 1.

According to the present invention, there is provided a method of labeling a component comprising, combining the component with an activated moiety having at least one N-hydroxynapthalimide-Rx group.

Those skilled in the art can appreciate that an N-oxynapthalimide ester can react with an amino or sulfhydryl group, on a nucleoside, nucleotide, solid support, carbohydrate, or protein.

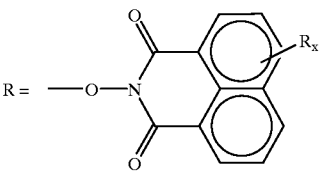

Rx can be hydrogen, sulfonyl and alkyl. When Rx is a polar moiety such as sulfonyl, those skilled in the art can appreciate the versatility in the increased solubility in water.

Figure 9:
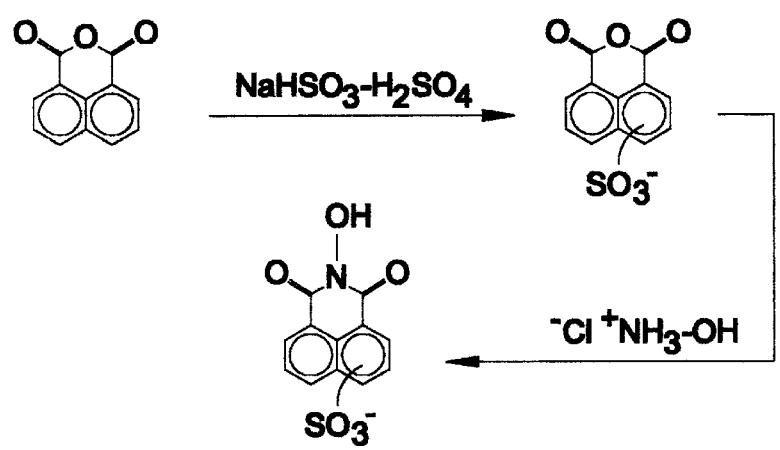
FIG. 9 is a schematic diagram outlining the steps for the synthesis of Sulpho-N-hydroxynaphthalimide.

According to the present invention, sulpho-N-hydroxynaphthalimide can be synthesized according to the scheme in FIG. 9 (E. L. Martin and L. F. Fieser; Organic Synthesis Coll. Vol., 3, 633, 1955; Fieser and Fieser, Reagent for Organic Synthesis, Volume 1, page 486, 1967, herein incorporated by reference in their entirety).

Typically, the component is selected from the group consisting of nucleosides, nucleotides, nucleoside triphosphates, dideoxynucleoside triphosphates, deoxynucleoside triphosphates, and derivatized versions of the foregoing. Further components include nucleic acids, DNA, derivatized nucleic acids, derivatized deoxynucleic acids, DNA fragments, RNA fragments, derivatized DNA fragments, and derivatized RNA fragments. Components can also include antibodies, proteins, peptides, enzyme substrates, hormones, lymphokines, metabolites, receptors, antigens, haptens, lectins, avidin, streptavidin, toxins, carbohydrates, oligosaccharides, polysaccharides, and other materials including drugs, toxins, blood cells, microbial materials, particles, plastic or glass surfaces, and polymer membranes.

The activated moiety typically can be biotin, hapten, cyanine dyes, merocyanine dyes, styryl dyes, fluorophores such as fluorescein, rhodamine, Texas red, chemiluminescent molecules such as acridinium esters, dioxitane derivatives, electroluminescent labels such as ruthenium based molecules, hapten molecules such as digoxigenin and chromophore molecules such as coumarins.

Cyanine Dyes

A series of new fluorescent labeling reagents based on cyanine dyes has been developed. We describe the synthesis and properties of these reagents. They contain N-hydroxynapthalimide ester reactive groups that can be readily conjugated to antibodies, avidin, DNA, lipids, polymers, and other amino-group containing materials. The labeling reagents are water soluble, less sensitive to pH, and show much reduced dye aggregation under labeling conditions.

The cyanine and related dyes according to the present invention are especially well adapted for the analysis of a mixture of components wherein dyes of a variety of excitation and emission wavelengths are required because specific cyanine and related dyes have a wide range of excitation and emission wavelengths. Specific cyanine and related dyes having specific excitation and emission wavelengths can be synthesized by varying the number of methine groups or by modification of the cyanine rings structures. Thus, it is possible to synthesize dyes having particular excitation wavelengths to correspond to a particular excitation light source, such as a laser, i.e. a He Ne laser or a diode laser.

The present invention relates to the covalent reaction of highly luminescent and highly light absorbing cyanine and related dye molecules under reaction conditions to amine, hydroxy, aldehyde, sulfhydryl or other groups on proteins, peptides, carbohydrates, nucleic acids, derivatized nucleic acids, lipids, certain other biological molecules, biological cells, as well as to non-biological materials such as soluble polymers, polymeric particles, polymer surfaces, polymer membranes, glass surfaces and other particles and surfaces.

Cyanine dyes have several desirable properties to serve as sensitive detection labels: Absorbance at longer wavelengths (which translates into the use of inexpensive detection systems and low background from biological samples at these wavelengths), high extinction coefficient, relatively high quantum efficiency, small molecular size, ease of chemical manipulation without compromising the fluorescence characteristics and reasonable stability to reagents, pH and temperature.

The spectral properties of the dyes of this invention are not appreciably altered by the functionalization described in this specification. The spectral properties of labeled compounds are also not very different from the basic dye molecule that has not been conjugated to the compound. The dyes described in this invention alone or conjugated to a labeled material generally have large extinction coefficients ($\in$~100,000 to 250,000), and emit light in the spectral range of 400 to 900 nm. Thus, they can be especially valuable as labeling reagents for luminescence detection.

The cyanine dyes have a general structure where the chromophore of the cyanine dyes is composed of a series of conjugated double bonds having two quaternary nitrogen atoms at the terminal ends, which share one positive charge. According to the number of central double bonds, the cyanine dyes can be classified as monocarbocyanine (n=1, also known as trimethinecarbocyanine), dicarbocyanine (n=2, also known as pentamethinecarbocyanine), and tricarbocyanine (n=3, also known as heptamethinecarbocyanine). A chemically reactive alkyl chain can be attached to the dye, which can be alkyl, alkylsulfonate, or alkylcarboxylate.

Cyanine dyes having the desired spectral characteristics can be predicted from several empirical rules. First, if an X group of gem-dimethyl is used as a reference, then an O substitution shifts the absorption and emission maxima about 50 nm to the shorter wavelength, whereas an S substitution shifts the absorption and emission maxima about 25 nm to the longer wavelength. Second, each conjugated double bond, n, added to the chromophore will shift the absorption and emission maxima about 100 nm to the longer wavelength. Thus, the maximum absorption is about 550 nm for n=1, about 650 nm for n =2, and about 750 nm for n=3. Third, each aromatic group on the side of the molecule will shift the absorption about 15 nm to the longer wavelength. Fourth, R groups, such as alkyl, alkyl sulfonate, and alkyl carboxylate, have little effect on the absorption and emission maxima.

A chemically reactive alkyl chain is attached to the nitrogen in the indole or benzoindole portion of the dye. The incorporation of at least one reactive functional group, such as a carboxylate or sulfonate group, into the basic cyanine structure permits covalent attachment of the dye to a nucleotide through the use of derived active esters. An optimum length of the attached alkyl chain having a reactive functional group, which will not interfere with base pairing or the incorporation of nucleotides into polynucleotides, can be determined empirically. The length of the attached alkyl chain is preferably about 3 to about 12 carbon atoms long. A most preferred alkyl chain is about 6 carbon atoms long.

The most preferred activated fluorescent dyes are shown in FIG. 1. The first pair of dyes, Cy5 (1) and DBCy5 (2) are dicarbocyanine dyes, while the second pair of dyes, Cy7 (3) and DBCy7 (4), are tricarbocyanine dyes. The difference between the two pairs of dyes is the presence of an additional double bond in Cy7 (3) and DBCy7 (4) relative to Cy5 (1) and DBCy5 (2). Consequently, the dicarbocyanine dyes have absorption and emission maxima about 100 nm shorter than their tricarbocyanine counterparts. The difference between Cy5 and Cy7 versus DBCy5 and DBCy7 is that the latter two dyes have two extra benzene group substitutions relative to the indole cyanines Cy5 and Cy7. Consequently, the absorption and emission maxima of the benzoindole cyanines, DBCy5 and DBCy7, are about 30 nm longer that their indole cyanine counterparts, Cy5 and Cy7. The sulfonate groups on the aromatic rings of the dyes have little or no effect on the chromophore, but do increase the hydrophilicity and charge density of the molecules.

Cy5 and Cy7 are commercially available from Amersham and BDL. Alternatively, cyanine dyes can be synthesized de novo, as previously described (R. J. Mujumder et al., Bioconjugate Chemistry, 4(2):105 (1993); and S. R. Mujumder et al., Bioconjugate Chemistry, 7(2):356 (1996); both of which are herein incorporated by reference) or as shown in FIGS. 2–5.

It is an object of the present invention to provide an activated dye having the formula:

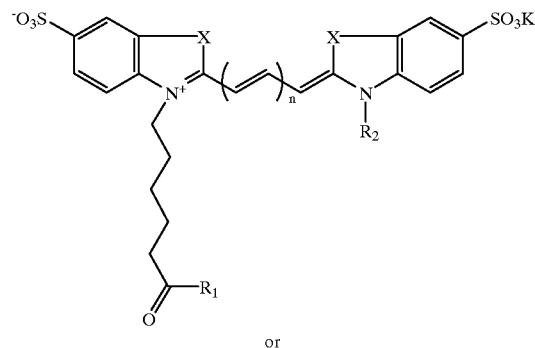

or

-continued

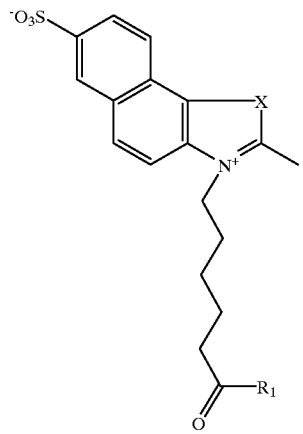

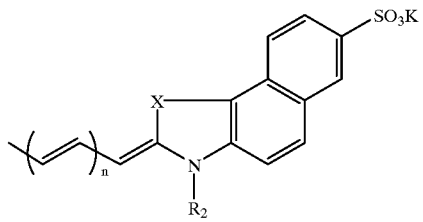

wherein n is 1, 2, or 3, X is S, O, N, CH$_2$, or C(CH$_3$)$_2$, R1 is N-oxynaphthalimide-Rx, and R2 is alkyl, alkylsulfonate, alkylcarboxylate, activated alkylsulfonate, or activated alkylcarboxylate having an alkyl chain about one to ten carbon atoms long, whereby Rx is selected from the group consisting of hydrogen, sulfonyl and alkyl.

Also provided, according to another embodiment of the present invention is a method of preparing an activated dye. The method comprising the steps of dissolving a cyanine dye having at least one carboxyl group in a solvent, and combining N-hydroxynaphthalimide-Rx or substituted derivatives and an activating agent with the dissolved cyanine dye to form an activated dye. Rx is selected from the group consisting of hydrogen, sulfonyl and alkyl. The activating agent can be CDI or DCC. Preferably, the cyanine dye is selected from the group consisting of Cy5, benzo-Cy5, dibenzo-Cy5, Cy7, benzo-Cy7, and dibenzo-Cy7.

Typically, the solvent comprises an organic solvent. Preferably, the solvent comprises dimethyformamide. Typically, the amount of N-hydroxynaphthalimide combined with the cyanine dye is at least about 2 molar equivalents. Preferably, the amount of N-hydroxynaphthalimide-Rx ranges from about 1.5 to about 5 molar equivalents.

The method can further comprise the additional step of precipitating the activated dye from the mixture. Preferably, the activated dye is precipitated by adding ethyl acetate.

Nucleotides

The nucleotides of the present invention are comprised of at least one phosphate group or its analog, a sugar, and a heterocyclic base. A triphosphate or close analog is essential to provide an acceptable substrate for an enzyme, such as DNA polymerase. Accordingly, triphosphates are most preferred.

The sugar is generally a five carbon furanose sugar, such as ribose, arabinose, or deoxyribose. Preferably, the sugar is a chain terminator that corresponds to the 2'-deoxyribofuranose portion of natural DNA polymerase substrates. Nucleotides that are chain terminators generally have a ribofuranose sugar that lacks a hydroxy group at the 3'-position that can be employed for chain elongation. Alternatively, a ribofuranose analog, such as arabinose, can be used for the sugar moiety of the nucleotide. The following modified furanose sugars can comprise a portion of the nucleotides of the present invention: 2'3'-dideoxy-β-D-ribofuranosyl, β-D-arabinofuranosyl, 3'-deoxy-β-D-ribofuranosyl, 3'-amino-2'3'-dideoxy-β-D-ribofuranosyl, 2'3'-dideoxy-3'-fluoro-β-D-ribofuranosyl, and 2'3'-dideoxy-2'3'-didehydro-β-D-ribofuranosyl. In addition, acyclic groups, such as 2-oxyethoxymethyl, can also be used as sugar moieties in chain terminating nucleotides.

The heterocyclic base portion of the nucleotides is generally a purine or pyrimidine base. Preferably the base portion is able to form hydrogen bonds as needed for accurate base-pairing during enzymatic DNA synthesis. This structural part can also carry the fluorescent dye. The 5-position on the pyrimidines and the 7-position on the purines may carry a relatively bulky substituent without significantly interfering with the overall binding or recognition of complementary bases during sequencing reactions. Consequently, the preferred heterocyclic bases include: uracil, cytosine, 7-deazaadenine, 7-deazaguanine, and 7-deazahypoxanthine. The unnatural 7-deazapurines are employed so that the fluorescent dye can be attached without adding a net charge to the base portion or destabilizing the glycosidic linkage. In addition, other heterocyclic bases, which are functionally equivalent as hydrogen donors and acceptors may be used.

Linker

A linker may be employed, which is simply an amino group alone or a chain with a backbone containing such atoms as carbon, nitrogen, oxygen, or sulfur. The linker is preferably an alkynylamino group in which one end of the triple bond is attached to an amine through a substituted or unsubstituted diradical moiety of 1–20 atoms as in U.S. Pat. Nos. 5,047,519 and 5,150,507, incorporated herein by reference. The other end of the triple bond is covalently attached to the heterocyclic base at the 5-position for pyrimidines or the 7-position for purines.

The linker must not significantly interfere with nucleotide binding to or incorporation by DNA polymerase. Taking into account the portion contributed by chemically reactive alkyl chain from the dye plus the additional diradical moiety interposed between the base and the reactive alkyl chain, the minimum number of atoms of the chain's backbone comprises about 10 atoms. While longer connecting chains are possible, the preferred length of the chain linking the base and the fluorescent dye is from about 13 to about 20 Å, which corresponds to a chain of about 10 to about 12 atoms.

Dye Attachment to Nucleotides

Fluorescent dyes can be attached to nucleotide monomers by combining amino-nucleotides with activated carboxylic acid esters of the dyes. Preparation of the activated cyanine dyes is accomplished by reaction of the dyes with an activating agent, such as carbonyl diimidazole (CDI, 2 molar equivalents/carbonyl group), in N,N-dimethylformamide (DMF) for 5 hours, followed by addition of 2 equivalents of N-hydroxynaphthalimide. The solution is stirred overnight, poured into ethyl acetate, and the resulting precipitate is collected by filtration to give the activated esters.

Conjugation of amino nucleoside triphosphates to the activated labels in organic medium The nucleoside triphosphates are typically synthesized as sodium or potassium or lithium salts. As such, they usually are not soluble in organic solvents. Accordingly, coupling of activated labels needs to be performed in aqueous systems, which can cause undesirable hydrolysis of the expensive activated labels and also results in lower yields.

According to one aspect of the present invention, the concept is provided of converting the triphosphate to trialkyl ammonium salts so that they will be soluble in organic solvents. This can be accomplished, for example, by converting a sodium salt of nucleoside triphosphate to a tributyl ammonium salt and then performing the coupling with Cy5-N-oxynapthalimide in organic solvent such as DMF. According to the present invention, converting nucleoside triphosphates to their tributyl ammonium salts gives conjugation products in substantially higher yield compared to preparations in an aqueous solvent. Further, by performing the reaction in an organic solvent, one skilled in the art can eliminate typical hydrolysis problems seen when the reaction is performed in an aqueous solvent. An added benefit in performing this reaction in an organic solvent is that less excess of the expensive labeling reagent is required, therefore it can be more economical.

Also provided according to the present invention is a method of labeling a nucleoside triphosphate. The method comprises the steps of, converting the nucleoside triphosphate to its trialkyl ammonium salt to form a nucleoside triphosphate trialkyl ammonium salt, and combining the nucleoside triphosphate trialkyl ammonium salt with an activated moiety having an activated ester group. The activated ester group can be selected from the group consisting of N-hydroxysuccinimide, paranitrophenol, N-hydroxyphthalimide, and N-hydroxynaphthalimide-Rx activated esters, wherein Rx is selected from the group consisting of hydrogen, sulfonyl and alkyl. Preferably, the activated moiety has at least one N-oxynaphthalimide-Rx group, wherein Rx is selected from the group consisting of hydrogen, sulfonyl and alkyl. The trialkyl ammonium salt is preferably a $C_1$–$C_{16}$ trialkyl ammonium salt. Suitable $C_1$–$C_{16}$ alkyl groups include methyl, ethyl, i-propyl, n-butyl, n-octyl, n-decanyl, n-hexadecyl, and the like. The most preferred trialkyl ammonium salt is a tributyl ammonium salt.

Preferably, the activated moiety is selected from the group consisting of biotin, hapten, cyanine dyes, merocyanine dyes, styryl dyes, fluorophores such as fluorescein, rhodamine, Texas red, chemiluminescent molecules such as acridinium esters, dioxitane derivatives, electroluminescent labels such as ruthenium based molecules, hapten molecules such as digoxigenin and chromophore molecules such as coumarins.

Preferably, the method is done in an organic solvent.

Oligonucleotides

As used herein, the term "oligonucleotide" is meant to encompass synthetic deoxy-and ribo-oligonucleotides as well as modified oligonucleotides i.e., where the 3'OH, 5'OH, sugar or heterocyclic base are modified, as well as modification of the phosphate backbone (e.g. methyl phosphonates, phosphorothioates, and phosphoramidates). Additionally, oligonucleotides can also include oligonucleotides comprising an attached reporter group, e.g. biotin, avidin, haptens, dyes, fluorescent, chemiluminescent, enzymatic or radioactive labels, and solid supports other than the solid support from which the oligonucleotide is synthesized.

In yet another embodiment of the present invention, there is provided a method of labeling an oligonucleotide, comprising modifying an oligonucleotide to contain a nucleophile, thereby forming a modified oligonucleotide, and combining the modified nucleotide with an activated dye having at least one N-hydroxynaphthalimide-Rx group, wherein Rx is selected from the group consisting of hydrogen, sulfonyl and alkyl. Typically, the modified oligonucleotide is an amino-oligonucleotide modified at the 5'-terminus.

Preferably, the activated dye is selected from the group consisting of:

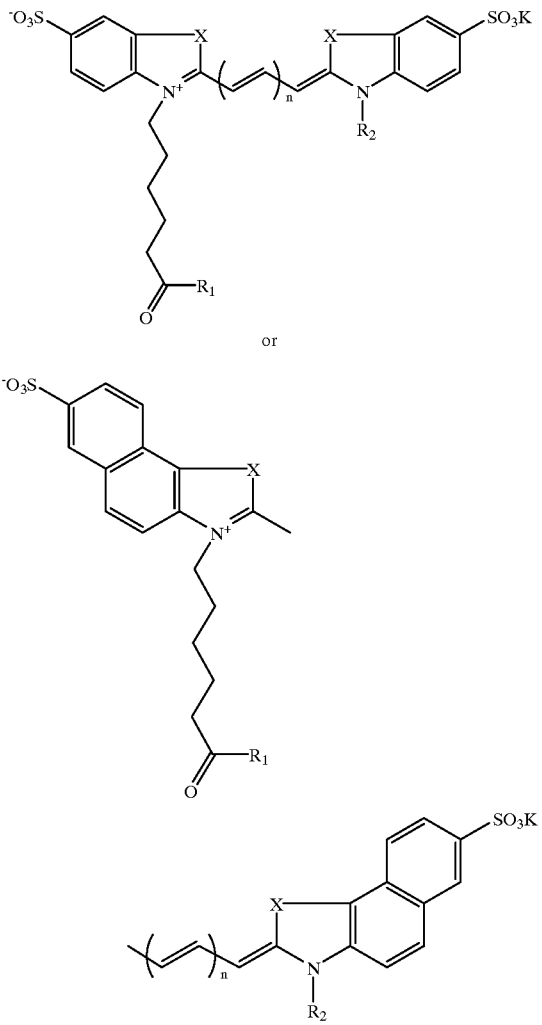

wherein n is 1, 2, or 3, X is S, O, N, $CH_2$, or $C(CH_3)_2$, R1 is N-oxynaphthalimide-Rx, and R2 is alkyl, alkylsulfonate, alkylcarboxylate, activated alkylsulfonate, or activated alkylcarboxylate having an alkyl chain about one to ten carbon atoms long, whereby Rx is selected from the group consisting of hydrogen, sulfonyl and alkyl.

The activated dyes can be combined with amino-oligonucleotides in a carbonate-bicarbonate buffer. The reaction can take place at room temperature for about 1 to 16 hours. The dye labeled nucleotides can then be purified by reverse phase HPLC.

Also provided according to the present invention is a method of labeling an oligonucleotide in organic solvent. The method comprises the steps of, converting the oligonucleotide to its trialkyl ammonium salt to form an oligonucleotide trialkyl ammonium salt, and combining the oligonucleotide trialkyl ammonium salt with an activated moiety having an activated ester group. The activated ester group can be selected from the group consisting of N-hydroxysuccinimide, paranitrophenol, N-hydroxyphthalimide, and N-hydroxynaphthalimide-Rx activated esters, wherein Rx is selected from the group consisting of hydrogen, sulfonyl and alkyl. Preferably, the activated moiety has at least one N-oxynaphthalimide-Rx group, wherein Rx is selected from the group consisting of hydrogen, sulfonyl and alkyl. The trialkyl ammonium salt is preferably a $C_1$–$C_{16}$ trialkyl ammonium salt. Suitable $C_1$–$C_{16}$ alkyl groups include methyl, ethyl, i-propyl, n-butyl, n-octyl, n-decanyl, n-hexadecyl, and the like. The most preferred trialkyl ammonium salt is a tributyl ammonium salt.

Applications of Cyanine Dye Labels in DNA Sequencing

The chain termination method of sequencing is based on in vitro DNA synthesis reactions in the presence of a primed DNA template, 2'deoxyribonucleoside triphosphates (dNTPs), and chain terminators, e.g. dideoxyribonucleoside triphosphates (ddNTPs). When the chain terminator is incorporated by a DNA polymerase into a growing polynucleotide chain, elongation is terminated. The DNA products are thus a series of polynucleotide chains complementary to the template with a specific chain terminator at the 3' end.

Accordingly, a preferred use for the fluorescent-labeled nucleotides and oligonucleotides of the present invention is in DNA sequencing, which involves labeling dideoxy terminators, nucleoside triphosphates, or oligonucleotide primers with a fluorescent label. Most preferably, each purine and/or pyrimidine base containing chain terminator used in the sequencing reaction is labeled with a different cyanine dye. Prematurely terminated DNA fragments resulting from sequencing reactions using such dye-labeled chain terminators are then differentially labeled at their 3' termini. Since each base has it's own distinguishable cyanine dye attached, a single sequencing reaction and a single separation lane can be used to sequence one template using one primer.

Dye-labeled deoxy- and dideoxy-nucleoside triphosphates can be prepared by the methods described herein. The preferred method comprises the steps of combining in a reaction mixture a tributyl ammonium salt of a chain terminating nucleoside triphosphate and an activated dye having at least one N-oxynapthalimide-Rx group.

While the dyes described herein are used to greatest advantage in the preparation of fluorescent-labeled chain terminators, they can also be used to label polynucleotides internally. In one version of this procedure, four separate sequencing reactions are set up, each having a single chain terminator and a single dye-labeled nucleoside triphosphate, which is not a chain terminator. The fluorescent-dye labeled DNA fragments produced in each sequencing reaction can be separated and detected individually. Alternatively, the sequencing reaction products are combined and the components of the multi-colored mixture are separated and detected in a single electrophoretic channel or capillary.

The labeled nucleotides described herein can also be used for labeling primers. The availability of activated derivatives of the dyes, as described in this application, allows one to design nucleoside phosphoramidites which are labeled with different cyanine dyes. When used in an automated synthesizer, such a reagent allows the final 5' residue and the fluorescent reporter to be introduced simultaneously.

More preferably, an activated cyanine dye is added to an oligonucleotide into which a primary amino group has been incorporated, usually at the 5' end. Synthesis of such modified oligonucleotides is typically achieved by adding a so-called amino-link or amino-modifier phosphoramidite as the last step in oligonucleotide synthesis, using the "labeling" method on the synthesizer. The fluorescent tag is added as an activated moiety, e.g., N-hydroxynaphthalimide-Rx-ester, to the oligonucleotide into which a primary amino or thiol group has been incorporated.

The fluorescent dye-labeled primers can then be used in separate sequencing reactions, which incorporate a single chain terminator into the reaction mixture. The fluorescent dye-labeled DNA fragments generated in separate sequencing reactions can be electrophoretically separated and detected individually. Alternatively, the reaction products can be combined and separated in a single electrophoretic channel or capillary.

Amplification

The fluorescent labeled nucleotides and oligonucleotides of the present invention can also be used to identify products of DNA amplification methods, such as the polymerase chain reaction (PCR). In "multiplex" PCR reactions, sequence specific primers, which are differentially labeled by the fluorescent dye labeled nucleotides of the present invention, may be used to direct the amplification of several different sequences of interest. The sequences of interest can then be identified by their fluorescence emission and/or their size.

The following Examples below illustrate important embodiments of the method according to the present invention.

EXAMPLES

Chemicals/Reagents

Chemicals and solvents were used as obtained from the vendors. The following reagents were obtained from Aldrich Chemical Co. (Milwaukee, Wis.): Acetic acid, acetic anhydride, carbonyl diimidazole (CDI), dichloromethane, dicyclohexylcarbodiimide (DCC), diethyl ether, dimethylformamide (DMF), ethyl acetate (EtOAc), isopropyl alcohol, malonaldehyde bis(phenylimine) monohydrochloride, methanol, pyridine, silica gel plates, sodium bicarbonate, sodium carbonate, tributylamine, triethylamine, trimethyl phosphate. DEAE Sephadex A-25 was from Pharmacia (Piscataway, N.J.). N-hydroxynaphthalimide and Glutaconaldehydedianil hydrochloride was from ACROS (Pittsburgh, Pa.).

Methods

All operations were conducted under either an inert atmosphere of commercial purified nitrogen or an anhydrous condition with a Drierite tube. The anhydrous solvents were purchased from Aldrich and were used without further purification. Reaction products were normally concentrated by rotary evaporation of volatile solvents at reduced pressure using a water aspirator.

UV-Vis spectra were recorded using either a Beckman DU-70 spectrophotometer, with a 1 cm path length quartz cell.

Proton nuclear magnetic resonance (NMR) spectra were recorded on a Brucker 300 (300 MHz) spectrometer. Unless otherwise stated, NMR spectra were run with DMSO-d6 as solvent and tetramethylsilane (TMS) as an internal standard. Chemical shifts are given in delta value ($\delta$) and coupling constants, J, in hertz (Hz).

High pressure liquid chromatography (HPLC) was performed using a Beckman model 100 A solvent delivery system equipped with a diode array detector.

Capillary Electrophoresis (CE) separations were performed on either a Beckman P/ACE™2000 equipped with UV detector or a Beckman P/ACE™5500 equipped with LIF detector. Beckman 635, 670, and/or 750 nm diode lasers were used with the P/ACE™5500 system. Capillary columns were bare fused silica, typically 27 cm length and 20–25 $\mu$m internal diameter (Polymicro Technologies, Phoenix, Ariz.). Running buffers were 100 mM or 150 mM sodium salt of boric acid, pH 10.2 or 8.5, respectively.

Synthesis of activated cyanine dyes

Activated monoacids of Cy5, Cy7, DBCy5, and DBCy7 were synthesized as depicted in FIGS. 2–5. The experimental procedure for the final and critical steps of preparation of N-hydroxynaphthalimide active dyes were conducted as follows.

Carboxyalkyl sulfocyanine dye was dissolved in dry DMF (100 mg of dye/2ml). Carbonyl diimidazole (2 molar equivalents/carbonyl group) was added and the mixture was stirred at room temperature for 5 hr under nitrogen atmosphere. N-hydroxynaphthalimide (2 molar equivalents) was added and the reaction mixture was stirred overnight (~16 hr.). After diluting the mixture with dry ethylacetate, the supernatant was decanted. The active ester was purified by redissolving in dry DMF and precipitating with ethylacetate. Nearly quantitative yields of cyanine active esters were obtained.

Conjugation of N-hydroxynaphthalimide activated dyes to oligonucleotides:

This example describes how N-hydroxynaphtalimide activated monoacids of Cy5 and Cy7 were conjugated to an oligonucleotide 24mer having a 5' amino-terminus. The desired oligonucleotide sequence was synthesized on an automated oligonucleotide synthesizer (Oligo 1000, Beckman-Coulter Inc., Fullerton, Calif.). The following steps were then performed:

1. 5'-amino modifier C6 (Glen Research 10-1906-90, Sterling, Va.) was coupled for 10 minutes on the instrument and complete the cycle was completed.
2. Monomethyltrityl (MMT) was removed from the amino modifier and the coupling efficiency was measured.
3. Cleavage and deprotection of the oligonucleotide was conducted using ammonia/methylamine (1/9).
4. The oligonucleotide was analyzed by CE and reverse phase HPLC.
5. The $Abs_{260nm}$ of the amino modified oligonucleotide was taken. Then the oligonucleotide was evaporated to dryness.
6. The oligonucleotide was then coevaporated to dryness with 250 µl of triethylammoniumbicarbonate buffer (pH 8.2–8.6) and then with 250 µl of deionized water.
7. The oligonucleotide was dissolved in 350 µl of deionized water, 50 µl of 1M bicarbonate buffer (pH 9.0) was added, as well as activated Cy5 dye (3mg dissolved in 100 µl of dry DMF). The reaction mixture was well mixed and left overnight at room temperature in dark.
8. The product was passed through NAP-25 column (Sephadex G-25 from Pharmacia) using 0.01 M $NH_4Oac$ buffer (pH 7.0) and the oligonucleotide was collected.
9. Approximately 100 µl of the above solution was analyzed by reverse phase C18 HPLC.
10. The residual solution was completely evaporated, dissolved in ~200 µl of water, and purified using semiprep C18 reverse phase HPLC. Elution conditions were as follows: Buffer B: 100% AcCN and Buffer A: 0.01 M $NH_4OAc$ buffer (pH 7.0), 0–20 min gradient to 15%B, 20–25 min gradient to 25%B, 25–27 min gradient to 50%B, 27–30 min 50%B, 30–35 min 0%B.
11. The eluate from HPLC was evaporated completely to dryness, dissolved in water, and the Abs 260nm was read.

Figure 6:
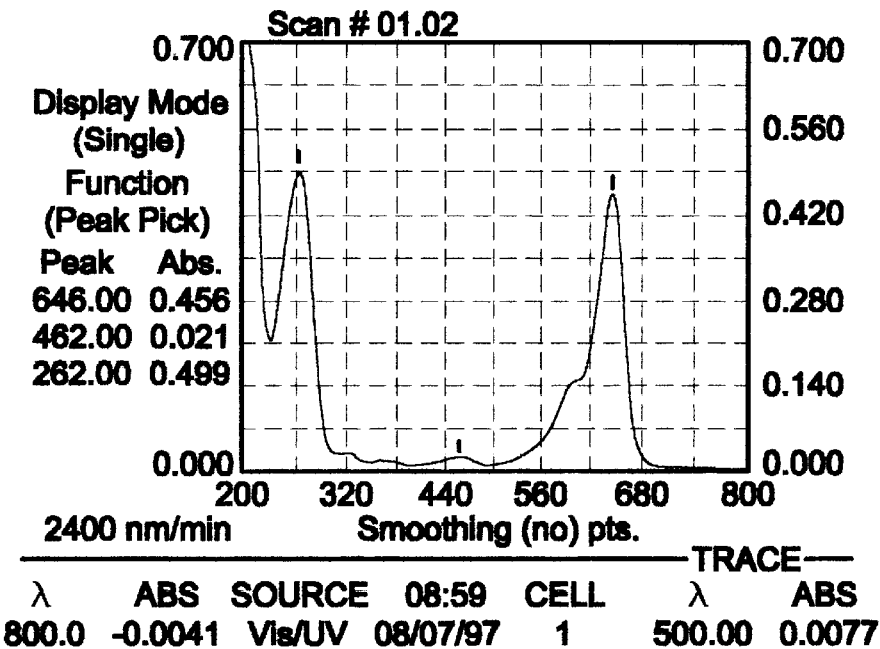
FIG. 6 is a Spectrophotometric Analysis of Cy5 labeled 24 mer.
Figure 7:
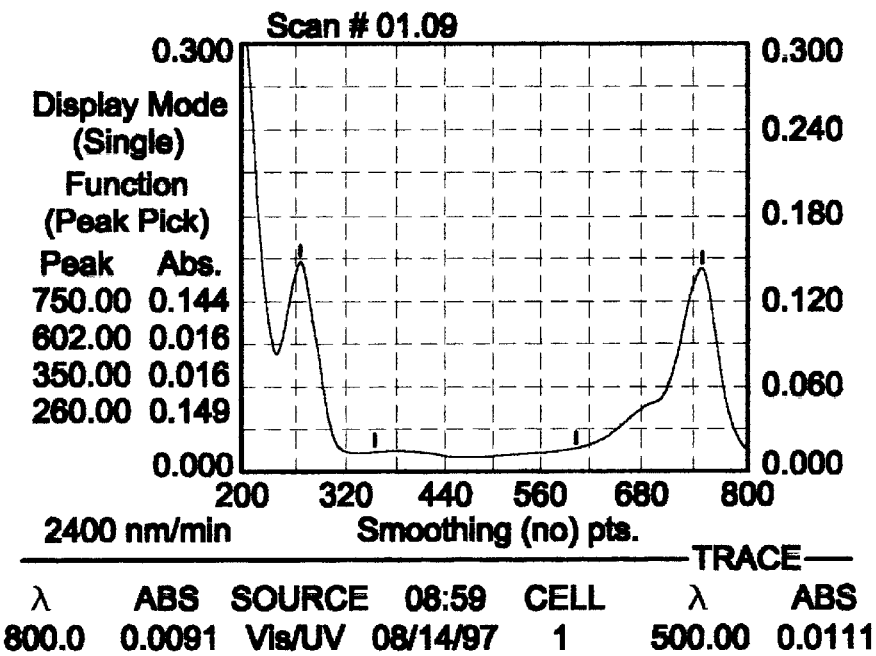
FIG. 7 is a Spectrophotometric Analysis of Cy7 labeled 24 mer.
Figure 8:
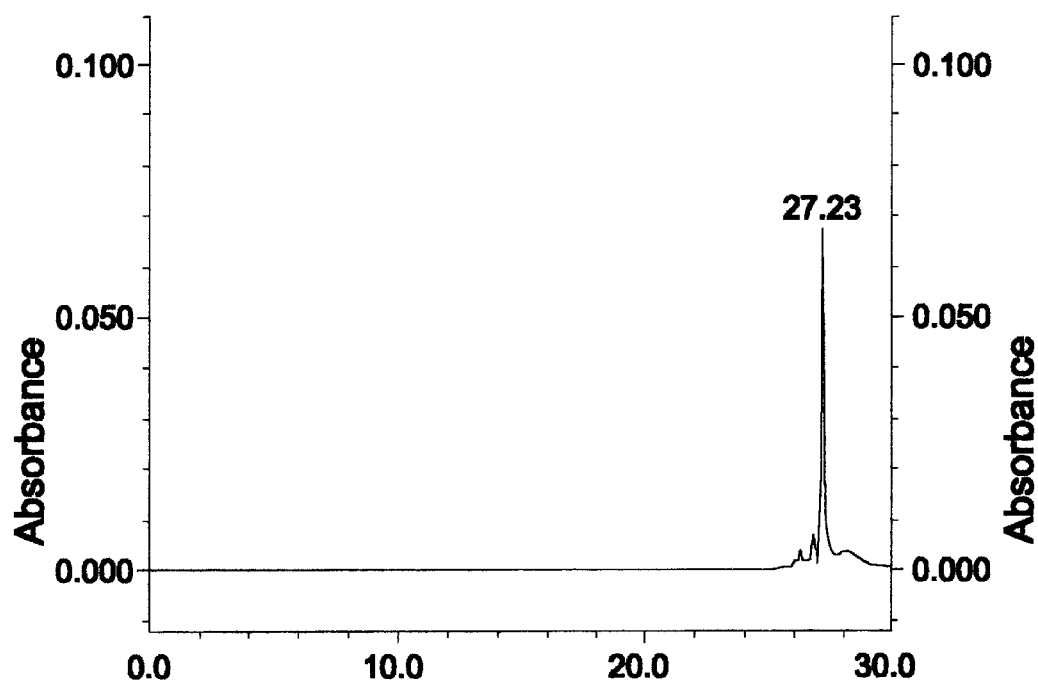
FIG. 8 is a Capillary Electropherogram of Cy5 labeled 24 mer.

The purified labeled oligo was analyzed by CE, CE-LIF, UV and HPLC. Some representative analytical data are presented in FIG. 6–8.

Comparison of N-hydroxynaphthalimide activated Cy5 with other activated esters

As the following data show, N-hydroxynapthalimide activated Cy5 gave higher yields than either N-hydroxynaphthalimide or N-hydroxysuccinimide. This result can be attributed to the increased stability of the activated ester in aqueous media in which the conjugation reaction is performed. The increased stability of N-hydroxynapthalimide activated Cy5 was confirmed in a separate experiment (shown below).

Comparison of the efficiencies of N-hydroxynaphthalimide activated Cy5 with N-hydroxynaphthalimide and N-hydroxysuccinimide activated Cy5 in conjugating to a 24 base oligonucleotide

| Excess reagent used | % overall yield with N-hydroxy-naphthalimide Cy5 | % overall yield with N-hydroxy-phthalimide Cy5 | % overall yield with N-hydroxy-succinimide Cy5 |
|---|---|---|---|
| 2x | 23.64% | 1.05% | 14.91% |
| 5x | 27.38% | 2.05% | 21.61% |
| 20x | 39.11% | 8.28% | — |
| 80x | 61.55% | 36.80% | — |

Stability of Activated Cy5 in DMF/HC03 buffer, pH 9.0 (1:4) by HPLC

| Time | Cy5-NHS | Cy5-Napththalimide |
|---|---|---|
| 30 min | 0.3% | 38.98% |
| 2 hr | 0.0% | 0.50% |

Biotin Activated esters

The following experimental results demonstrate that N-hydroxynaphthalimide activated esters can also be utilized to label a 5 'amino-oligonucleotide with biotin.

Comparison of the efficiencies of N-hydroxynaphthalimide activated Biotin with N-hydroxysuccinimide activated Biotin in conjugation to a 24 base oligonucleotides:

| Excess reagent used | % yield with N-hydroxysuccinimide | % yield with N-hydroxynaphthalimide |
|---|---|---|
| 2x | 28.14% | 58.62% |
| 5x | 50.48% | 61.84% |
| 20x | 63.41% | 74.20% |

It is obvious that napthalimide active esters resulted in higher yields. It requires the use of less excess reagent to obtain desired yields.

Conjugation of N-hydroxynaphthalimide activated Cy5 to an aminonucleoside

The following table compares the experimental results obtained when two different activated esters of Cy5 were conjugated to 5'-amino-5'-deoxythymidine in aqueous media. As shown in the following data, N-hydroxynaphthalimide activated Cy5 (Cy5-NAPH) gave higher yields than a N-hydroxysuccinimide activated Cy5 (Cy5-NHS).

Comparison of the efficiencies of N-hydroxynaphthalimide activated Cy5 with N-hydroxysuccinimide activated Cy5 in conjugation to a 5'-amino 5'deoxythymidine

| Time for reaction | % yield of conjugate | |
|---|---|---|
| | Cy5-NHS | Cy5-NAPH |
| 1 min | 29.81% | 6.09% |
| 30 min | 32.29% | 44.35% |
| 1 hr | 33.95% | 53.58% |
| 16 hr | 34.37% | 62.55% |

It is noteworthy that Cy5-NHS reacts fast initially and at the same time goes through an undesirable spontaneous aqueous hydrolysis faster thereby depleting the active species. On the other hand, Cy5-NAPH is more stable to aqueous hydrolysis and hence stays active in aqueous media ultimately resulting in higher yields.

Conversion of nucleoside triphosphates sodium salt or ammonium salt to nucleoside tributyl ammonium salt (for use in coupling in organic solvents).

The following procedure was used to prepare nucleoside triphosphates that can be labeled with N-hydroxynaphthalimide activated esters of cyanine dyes in organic media 1. Prewash ion-exchange resin (Dowex 50w-8X, H⁺form, 200–400 mesh) with (1:1) Methanol, 4 times.
2. Pack the resin in a column, wash with water 4 times and then with pyridine 4 times to convert the resin to a pyridinium form.
3. Dissolve the nucleoside triphosphate in water, apply to the column and elute the pyridinium form of triphosphate with water.
4. Check the fractions by TLC.
5. Pool the fractions in a round bottom flask and add 6 molar equivalents of tributylamine.
6. Evaporate at 30° C. Coevaporate the oily syrup with pyridine 2 times and then with DMF 2 times. Dissolve the resulting tributyl ammonium salt in DMF/pyridine (2:1) and store in the freezer.
7. The tributyl ammonium salt is ready for coupling to activated dyes in organic medium.

Synthesis of dye labeled dideoxynucleoside triphosphate terminators in organic medium The following reaction scheme summarizes the procedure used to couple dideoxynucleoside triphosphates to cyanine dyes in organic solvents.

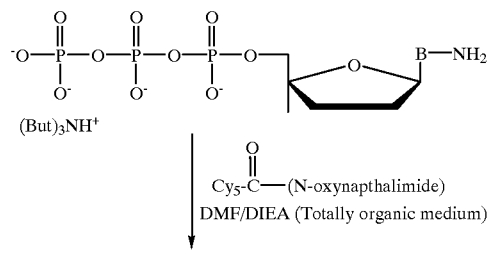

-continued

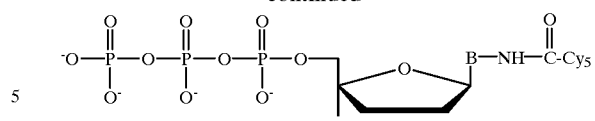

The active ester (2.0 μmol) of fluorescent dye was placed in a vial. A solution of the tributyl ammonium salt of triphosphate nucleotide terminator in anhydrous DMF (0.02 M, 1.0 μmol) was added, followed by the addition of 5μl of diisopropylethylamine (DEA). The vial was vortexed and allowed to stand in the dark at room temperature for 15 hr. The reaction mixture was analyzed by CE-LIF, to monitor the formation of the conjugate. The product was purified on reverse phase HPLC using the following conditions:

| Column: | Beckman C18 Ultrasphere (10 mm × 25 mm) |
|---|---|
| Flow rate: | 4 ml/min |
| Wavelength: | 260 nm and 598 nm |
| Eluents: | Solvent A: 0.1 M NH₄OAc |
| | Solvent B: Acetonitrile |

| Gradient: | | |
|---|---|---|
| Time (min) | A (%) | B (%) |
| 0 | 100 | 0 |
| 25 | 50 | 50 |
| 28 | 50 | 50 |
| 30 | 100 | 0 |
| 32 | 100 | 0 |

The product collected from the HPLC was assayed by CE-LIF, fluorometer, and enzyme digestion with alkaline phosphatase.

The present invention described herein has many advantages. The advantages include the discovery of N-hydroxynapthalimide and substituted N-hydroxynapthalimide as activating agents. Also included are methods for synthesizing activated esters of labeling compounds in a simple, fast, efficient manner with high yields. In addition, the methods provided for synthesizing labeled nucleotides in organic media reduces the spontaneous hydrolysis of the active species. The versatility of these activating agents in a variety of applications, especially when coupled to cyanine dyes, make these compounds especially valuable.

Although the present invention has been described in considerable detail with reference to certain preferred versions, other versions are possible. Thus, the spirit and scope of the appended claims should not be limited to the description of the preferred version contained herein.

What is claimed is:

1. An activated dye having the formula:

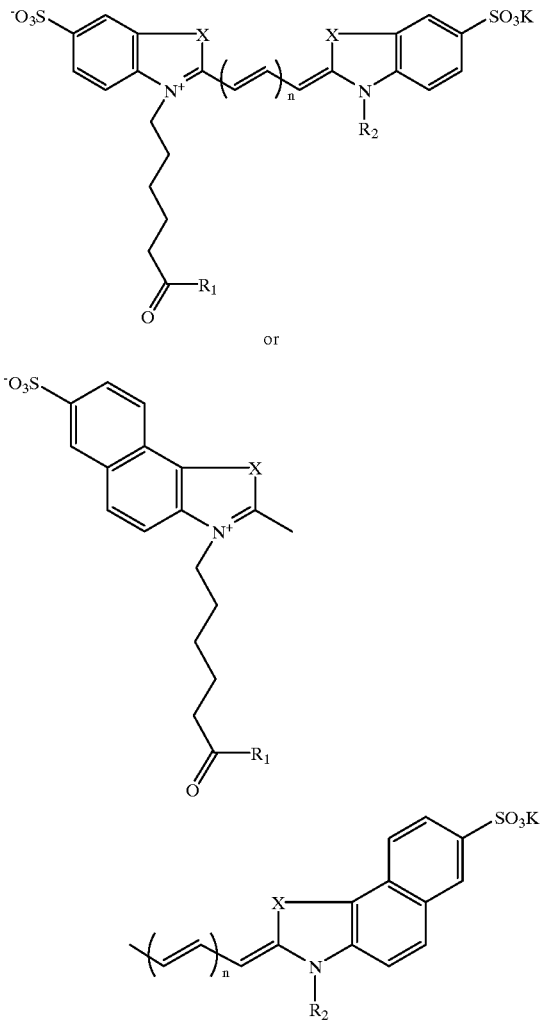

wherein n is 1, 2, or 3, X is S, O, N, $CH_2$, or $C(CH_3)_2$, R1 is N-oxynaphthalimide-Rx, R2 is alkyl, alkylsulfonate, alkylcarboxylate, activated alkylsulfonate, or activated alkylcarboxylate having an alkyl chain about one to ten carbon atoms long, whereby Rx is selected from the group consisting of hydrogen, sulfonyl, and alkyl.

2. A method of preparing an activated dye, the method comprising the steps of:
dissolving a cyanine dye having at least one carboxyl group in a solvent; and
combining N-hydroxynaphthalimide-Rx, wherein Rx is selected from the group consisting of hydrogen, sulfonyl, and alkyl, and an activating agent, with the dissolved cyanine dye to form an activated dye.

3. The method of claim 2, wherein the cyanine dye is selected from the group consisting of Cy5, benzo-Cy5, dibenzo-Cy5, Cy7, benzo-Cy7, and dibenzo-Cy7.

4. The method of claim 2, wherein the solvent comprises an organic solvent.

5. The method of claim 2, wherein the solvent comprises dimethyformamide.

6. The method of claim 2, wherein the amount of N-hydroxynaphthalimide combined with the cyanine dye is about two or more molar equivalents.

7. The method of claim 6, wherein the amount of N-hydroxynaphthalimide-Rx ranges from about 1.5 to about 5 molar equivalents.

8. The method of claim 2, further comprising the additional step of precipitating the activated dye from the mixture.

9. The method of claim 8, wherein the activated dye is precipitated by adding ethyl acetate.

10. A method of labeling an oligonucleotide, the method comprising the steps of:
modifying an oligonucleotide to contain a nucleophile thereby forming a modified oligonucleotide;
combining the modified oligonucleotide with an activated dye having at least one N-hydroxynaphthalimide-Rx group, wherein Rx is selected from the group consisting of hydrogen, sulfonyl, and alkyl.

11. The method of claim 10, wherein the nucleophile is an amino or thiol group.

12. The method of claim 10 wherein the modified oligonucleotide is an amino-oligonucleotide.

13. The method of claim 10 wherein the terminus of the oligonucleotide is modified.

14. The method of claim 10, wherein the activated dye is selected from the group consisting of:

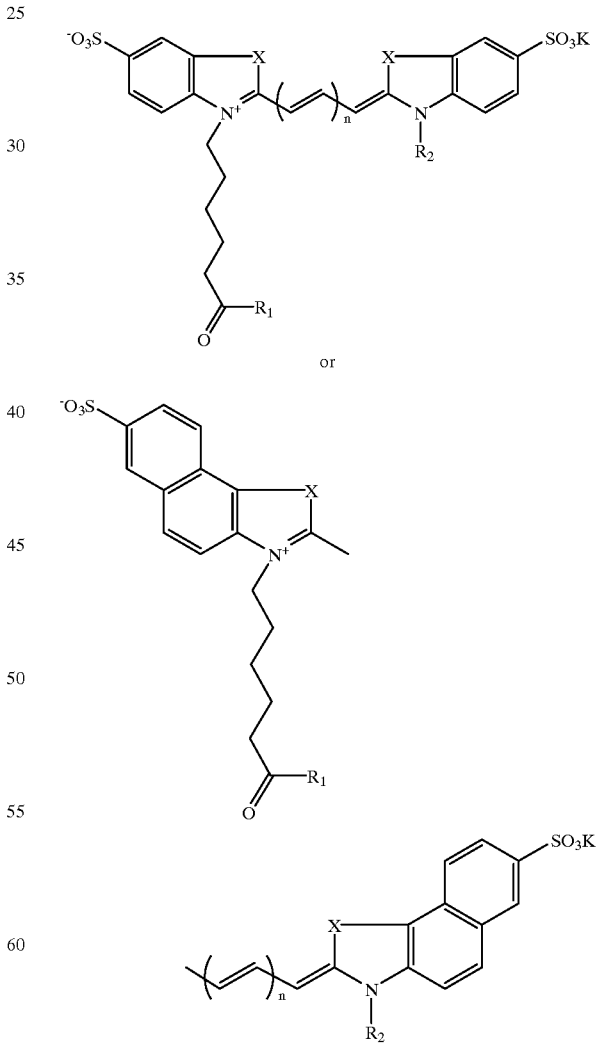

wherein n is 1, 2, or 3, X is S, O, N, $CH_2$, or $C(CH_3)_2$, R1 is N-oxynaphthalimide-Rx, R2 is alkyl, alkylsulfonate, alkylcarboxylate, activated alkylsulfonate, or activated alkylcarboxylate having an alkyl chain about one to ten carbon atoms long, whereby Rx is selected from the group consisting of hydrogen, sulfonyl, and alkyl.

15. The method of claim 10, wherein the activated dye is combined in molar excess relative to the modified nucleotide.

16. A method of labeling a component comprising, combining the component with an activated moiety having at least one N-hydroxynapthalimide-Rx group, wherein Rx is selected from the group consisting of hydrogen, sulfonyl and alkyl.

17. The method of claim 16, wherein the component is selected from the group consisting of antibodies, proteins, peptides, enzyme substrates, hormones, lymphokines, metabolites, receptors, antigens, haptens, lectins, avidin, streptavidin, toxins, carbohydrates, oligosaccharides, polysaccharides, and other materials including nucleic acids, DNA, derivatized nucleic acids, derivatized deoxynucleic acids, DNA fragments, RNA fragments, derivatized DNA fragments, derivatized RNA fragments, drugs, toxins, blood cells, microbial materials, particles, plastic or glass surfaces, polymer membranes, nucleotides, deoxynucleotides, and dideoxynucleotides.

18. The method of claim 16, wherein the activated moiety is selected from the group consisting of biotin, hapten, cyanine dyes, merocyanine dyes, styryl dyes, fluorophores, fluorescein, rhodamine, Texas red, chemiluminescent molecules, acridinium esters, dioxitane derivatives, electroluminescent labels, ruthenium based molecules, hapten molecules, digoxigenin, chromophore molecules and coumarins.

19. A method of labeling a nucleoside triphosphate comprising, combining a nucleoside triphosphate having a nucleophilic group with an activated moiety having at least one N-hydroxynapthalimide-Rx group, wherein Rx is selected from the group consisting of hydrogen, sulfonyl and alkyl.

20. The method of claim 19, wherein the nucleophilic group is an amino group.

21. The method of claim 19, wherein the activated moiety is selected from the group consisting of biotin, hapten, cyanine dyes, merocyanine dyes, styryl dyes, fluorophores, fluorescein, rhodamine, Texas red, chemiluminescent molecules, acridinium esters, dioxitane derivatives, electroluminescent labels, ruthenium based molecules, hapten molecules, digoxigenin, chromophore molecules and coumarins.

22. A method of labeling a nucleoside triphosphate, the method comprising the steps of:

converting the nucleoside triphosphate to its trialkyl ammonium salt to form a nucleoside triphosphate trialkyl ammonium salt; and combining the nucleoside triphosphate trialkyl ammonium salt with an activated moiety having an activated ester group.

23. The method of claim 22, wherein the trialkyl ammonium salt is a tributyl ammonium salt.

24. The method of claim 22, wherein the activated ester group is selected from the group consisting of N-hydroxysuccinimide, paranitrophenol, N-hydroxyphthalimide, and N-hydroxynaphthalimide-Rx activated esters, wherein Rx is selected from the group consisting of hydrogen, sulfonyl and alkyl.

25. The method of claim 22, wherein the activated moiety is selected from the group consisting of biotin, hapten, cyanine dyes, merocyanine dyes, styryl dyes, fluorophores, fluorescein, rhodamine, Texas red, chemiluminescent molecules, acridinium esters, dioxitane derivatives, electroluminescent labels, ruthenium based molecules, hapten molecules, digoxigenin, chromophore molecules and coumarins.

26. The method of claim 22, wherein the method is performed in an organic solvent.

27. A method of preparing a dye labeled dideoxynucleotide triphosphate terminator, the method comprising step of:

combining in a reaction mixture, a tributyl ammonium salt of a triphosphate nucleotide terminator; and an activated dye having at least one N-hydroxynapthalimide-Rx group.

28. A method of labeling an oligonucleotide, the method comprising the steps of:

converting the oligonucleotide to its trialkyl ammonium salt to form an oligonucleotide trialkyl ammonium salt; and combining the oligonucleotide trialkyl ammonium salt with an activated moiety having at least one activated ester group.

29. The method of claim 28, wherein the activated moiety is selected from the group consisting of biotin, hapten, cyanine dyes, merocyanine dyes, styryl dyes, fluorophores, fluorescein, rhodamine, Texas red, chemiluminescent molecules, acridinium esters, dioxitane derivatives, electroluminescent labels, ruthenium based molecules, hapten molecules, digoxigenin, chromophore molecules and coumarins.

30. The method of claim 28, wherein the method is performed in an organic solvent.

31. The method of claim 28, wherein the trialkyl ammonium salt is a tributyl ammonium salt.

32. The method of claim 28, wherein the activated ester group is selected from the group consisting of N-hydroxysuccinimide, paranitrophenol, N-hydroxyphthalimide, and N-hydroxynaphthalimide-Rx activated esters, wherein Rx is selected from the group consisting of hydrogen, sulfonyl and alkyl.

33. The method of claim 2, wherein the activating agent is selected from the group consisting of carbonyl diimidazole and dicyclohexylcarbodiimide.

* * * * *